United States Patent
Sieracki et al.

[11] Patent Number: 6,115,119
[45] Date of Patent: Sep. 5, 2000

[54] DEVICE AND METHOD FOR STUDYING PARTICLES IN A FLUID

[75] Inventors: Christian K. Sieracki; Michael E. Sieracki, both of Edgecomb; Charles S. Yentsch, West Boothbay Harbor, all of Me.

[73] Assignee: Bigelow Laboratory for Ocean Science, West Boothbay Harbor, Me.

[21] Appl. No.: 09/176,678

[22] Filed: Oct. 21, 1998

Related U.S. Application Data
[60] Provisional application No. 60/064,829, Oct. 21, 1997.

[51] Int. Cl.[7] .................................................. G01N 21/00
[52] U.S. Cl. ........................................................... 356/337
[58] Field of Search ............................... 356/337, 23, 39, 356/246, 28, 318, 335; 73/861.05; 382/134; 702/21, 29

[56] References Cited

U.S. PATENT DOCUMENTS

| | | | |
|---|---|---|---|
| 4,612,614 | 9/1986 | Deindoerfer et al. | 356/335 |
| 5,159,397 | 10/1992 | Kosaka et al. | 356/73 |
| 5,159,398 | 10/1992 | Maekawa et al. | 356/73 |
| 5,247,339 | 9/1993 | Shinichi | 356/73 |
| 5,247,340 | 9/1993 | Shinichi | 356/73 |
| 5,248,451 | 9/1993 | Tsunaga et al. | 252/512 |
| 5,471,294 | 11/1995 | Shinichi | 356/73 |

*Primary Examiner*—Frank G. Font
*Assistant Examiner*—Tu T. Nguyen
*Attorney, Agent, or Firm*—Pierce Atwood; Patrick R. Scanlon

[57] ABSTRACT

The present invention provides a device for studying particles in a fluid that advantageously allows particles having a broad range of particle size, e.g., in the 3–1000 $\mu$m range, to be readily imaged and counted.

17 Claims, 12 Drawing Sheets

DEVICE AND METHOD FOR STUDYING PARTICLES IN A FLUID

CROSS REFERENCE TO RELATED APPLICATIONS

This application claims the benefit of U.S. Provisional Application No. 60/064,829, filed Oct. 21, 1997.

BACKGROUND OF THE INVENTION

The present invention relates to a device and method for studying particles in a fluid.

Microscopic marine particles can dramatically affect, and be affected by, water properties. For example, marine particles have been shown to be indicators of water properties such as pollution, nutrient distribution and water mass boundaries. They have also been shown to control significant properties of water including fluorescence, oxygen and nitrogen content, opacity and light attenuation. Finally, marine particles are living at the very bottom of the food web, and thus can dramatically affect life all the way up the food chain. Thus, it is important to fully understand the properties and distributions of the particles present in water.

Several instruments are available to study individual marine biological particles, including in-situ, on-vessel, and laboratory instruments. However, the currently available instrumentation that is used for marine particle analysis has limitations. Currently, because it is difficult to achieve a sufficient flow rate to enable accurate counting of cells while retaining imaging capability, there has been an ongoing need for instrumentation capable of analyzing and imaging marine particles in the 3–1000 $\mu$m range both in the lab and on board a vessel.

SUMMARY OF THE INVENTION

The present invention provides a device for studying particles in a fluid that advantageously allows particles having a broad range of particle size, e.g., in the 3–1000 $\mu$m range, to be readily imaged and counted The device includes optics which provide an excellent depth of field, allowing the use of a "deep" sample chamber and high flow rate to enable the user to image particles in a relatively large sample of flowing fluid accurately and quickly. In preferred embodiments, the device includes software capable of storing and analyzing the images thus obtained, eliminating the need for manual counting and visual inspection of the particles. Moreover, in preferred devices, recording of an image is triggered by fluoresce or scattered light from a particle in the field of view, thus eliminating imaging of portions of fluid which contain no particles.

The device of the invention can be used to image marine particles or other biological particles in a fluid, and is suitable for use in a laboratory or in other environments, for example onboard a vessel.

In one aspect, the invention features a device for studying particles in a fluid that includes a depth of focus enhancer, an optical device including a unique binary optical element which increases the depth of focus of the imaging system.

In another aspect, the invention features a device for studying particles in a fluid that includes a triggering mechanism whereby particle fluorescence or scattered light triggers a signal which results in the imaging of particles passing through the flow chamber.

In another aspect, the invention features devices for studying particles, including computer algorithms that acquire particles images, generate size and scattered light and fluorescence files, and perform interactive scattergram functions. The interactive scattergram functions provide a size/fluorescence light graph ("scattergram") plotting particle data and allow the user to select a region of the scattergam, e.g., with a computer mouse, and display images of particles with properties in the selected region.

The invention also features methods of using the above devices.

Other features and advantages of the invention will be apparent from the description of the preferred embodiments thereon, taken together with drawings.

DETAILED DESCRIPTION OF THE PREFERRED EMBODIMENTS

Figure 1:
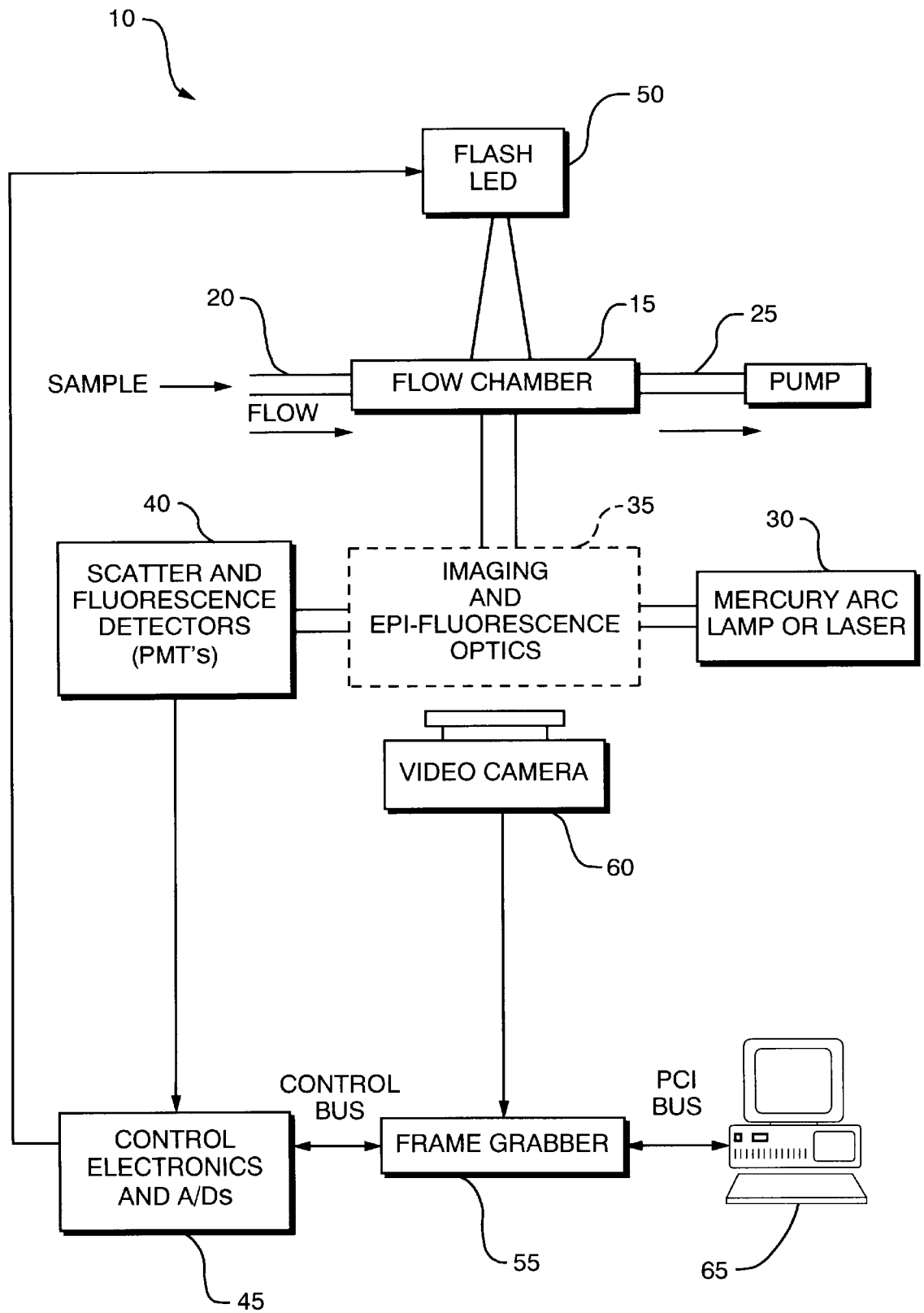
FIG. 1 schematically illustrates a device for studying particles in a fluid according to one embodiment of the invention
Figure 1A:
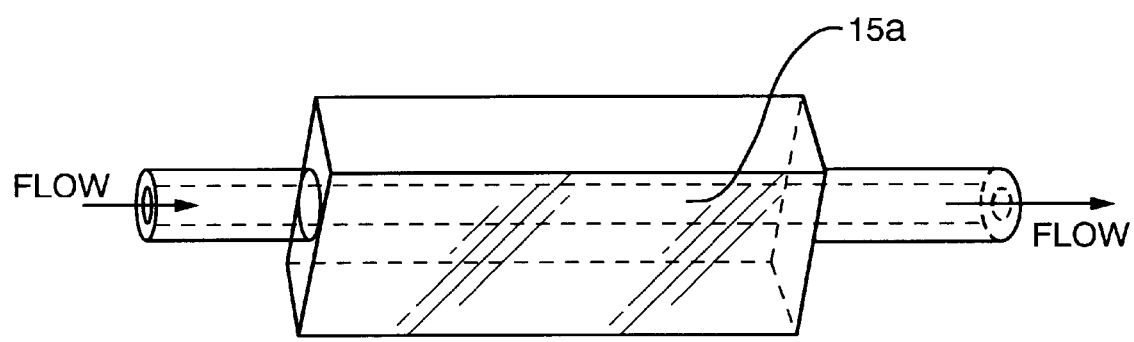
FIG. 1a is an enlarged perspective view of the flow chamber of the device of FIG. 1.

FIG. 1 shows a system 10 for the automated counting and sizing of marine particles. The system 10 includes a low fluorescence flow chamber 15 (i.e., a flow chamber formed of a material that does not readily fluoresce, e.g., microscope glass and low-fluorescence UV curable optical grade epoxy adhesive), including an inlet 20 and an outlet 25. The flow chamber 15 defines a channel 15a (shown in FIG.. 1a) through which a particle-containing fluid flows at a predetermined rate.

A light source 30 is used to generates fluorescence and scatter excitation light which is passed through the imaging optics 35 to the flow chamber 15, resulting in particle fluorescence and/or light scatter. The light source is preferably a mercury arc lamp with 440 nm excitation filter 33, or alternatively a 488 nm laser. Any particle fluorescence emissions from the flow chamber 15 (FIG. 1, 2) that have a wavelength of 535 to 900 nm are monitored with the system emission filters 43 and a high sensitivity photomultiplier tube (PMT) 40. The PMT output is processed by detection electronics 45. Preferably, the detection electronics 45 are provided with user-adjusted gain and threshold settings which determine the amount of fluorescence or scatter required for the system to acknowledge a passing particles.

If a sufficiently fluorescent particle passes through the flow chamber 15 a PMT fluorescence signal is sent to the detection electronics 45, which then generate a trigger signal (See FIG. 3, discussed below). The detection electronics 45 also preferably include a mechanism whereby the user may alternatively select a setting which automatically generates a trigger signal every second. The trigger signal causes a very high intensity LED flash 50 to backlight the flow chamber 15 and image the passing particles. The very high intensity LED flash 50 is preferably a 670 nm LED which is flashed under the flow chamber for 200 μsec (or less) to capture an instantaneous image of the particles in flow on a video camera 60, which is positioned above the flow chamber 15. The trigger signal also causes a framegabber 55 and video camera 60 to image the flow chamber 15 while the LED flash 50 is occurring, allowing the framegrabber 55 to acquire this image immediately. The computer 65 may then measure the particle and store the data for later analysis.

The detection electronics 45 provide an amplified version of the PMT fluorescence signal to the analog-to-digital converter of computer 65. The software of computer 65 monitors the amplified version of the PMT fluorescence signal before, during and after the fluorescent events determine the peak fluorescence of each triggering particle. As will be discussed in detail below, with reference to FIG. 4, when a fluorescent particle is detected, the software scans the resulting image, separating the different particle The image of each particles is extracted from the image of the flow chamber 15 an inserted in a file. A special file is used to store the information on each particle, including the file location of the particle image, the particle size, fluorescence and time of particle passage.

Imaging Optics

Figure 2:
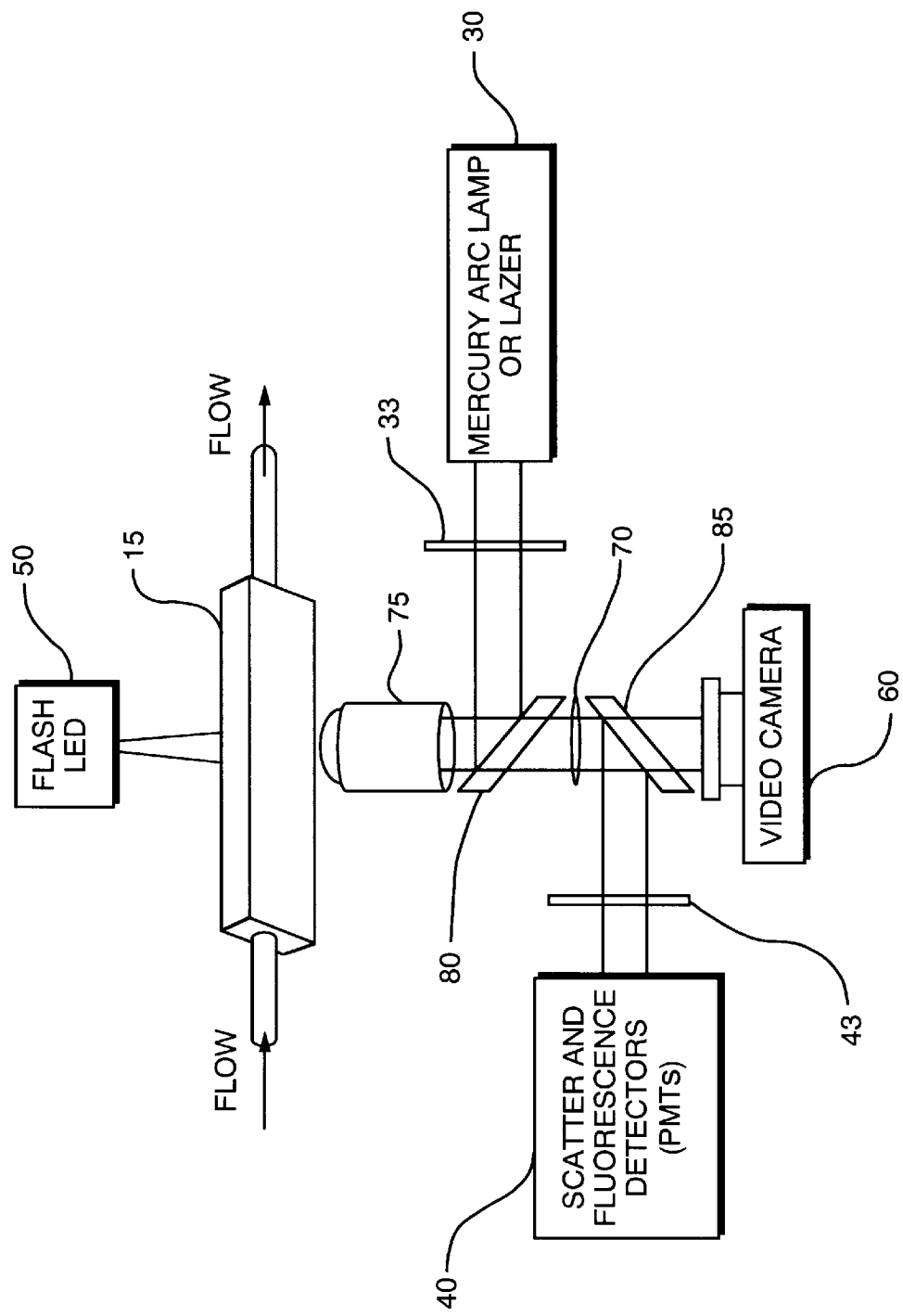
FIG. 2 is a view of the device of FIG. 1, with portions of the device omittede for clarity, and with a detailed view of the optics in the device.

FIG. 2 is a schematic view of the epi-fluorescence and imaging optics 35 (shown as a "black box " in FIG. 1). The imaging optics 35 include, but are not limited to, a 0.12 numerical aperture 4× microscope objective 75 to image the particle flow onto the video camera 60, focus fluorescence excitation light from the light source 30 onto the flow chamber 15 and focus the resulting particle fluorescence or scattered light onto the system PMT 40. A dichroic mirror 80 prevents the light from the light source 30 from reflecting back from the flow chamber 15 into the video camera 60. A partial mirror 85 splits the light from the light source 30, directing some of the light (preferably about 50%) to the video camera 60 and the remainder of the light to the PMT 40. A dichroic mirror may be used in place of the partial mirror 85.

The length and width of channel 15*a* of flow chamber 15 are selected to exactly match the field of view of the imaging optics 35 (1 mm across and 1 mm deep). This keeps all of the particles flowing through the flow chamber in focus, removing the need for a focussing sheath flow, and thereby enabling accurate counting of cells while retaining imaging capability. A depth of focus enhancer 70 is used with the objective 75 to increase the system depth of focus. Preferably, the depth of focus enhancer is designed to increase the depth of focus to match the channel depth. The depth of focus enhancer 70 allows the use of a thick flow chamber 15 with a high flow rate (e.g., up to 10 ml per minute) while maintaining very high image resolution without the depth of focus enhancer 70, the desired depth of focus would be difficult to attain without decreasing the system numerical aperture by a factor which would degrade the resolution and decrease the light throughput of the system, making it difficult to detect particle fluorescence.

Depth of Focus Enhancer

Figure 2A:
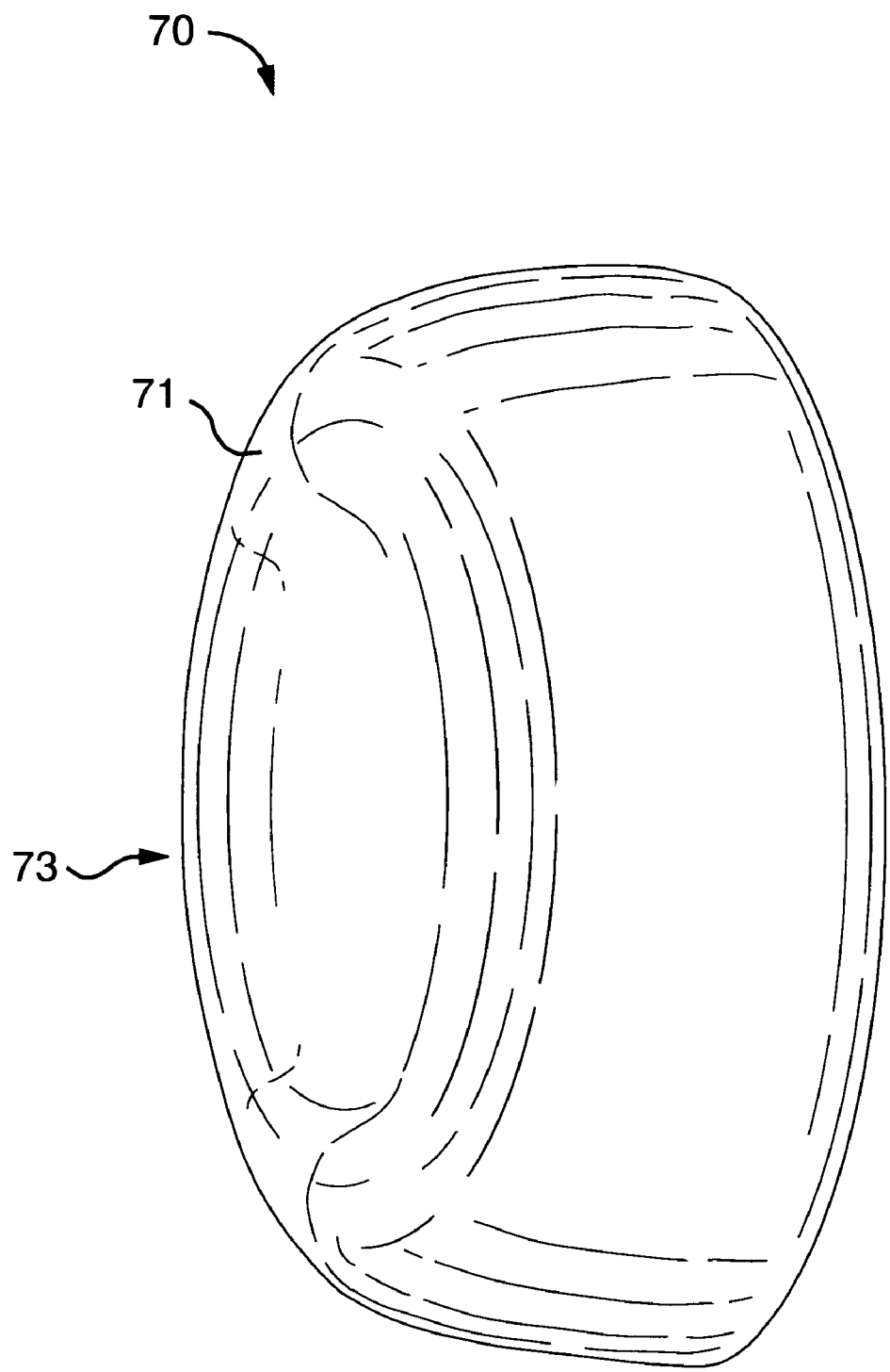
FIG. 2a is a view of the depth of focus enhancer included in the optics in FIG. 2.

FIG. 2*a* is an enlarged view of the depth of focus enhancer 70 included in the optics in FIG. 2. The depth of focus enhancer is an optical element that imparts a prescribed phase delay onto an incident wave-front through materials of varying thicknesses and possibly with different indices of refraction. The optical components which impart the phase delay are normally made of ground and polished glass. The shape of the optical element is shown in FIG. 2*a*. Preferably, the element is configured to impart a phase delay on incident light such that the microscope objective has a continuum of foci rather than a single focus. This may be accomplished by an element which imparts spherical aberration to the lens.

The depth of focus enhancer 70 is preferably a "binary optical element", an optical element fabricated by etching the desired phase delay into a glass substrate by a series of photolithographic exposure and etch steps. The rest is that a quantized version of the desired waveform is etched into the glass.

A binary optical element is fabricated by a series of etches where material in the substrate glass is etched a prescribed depth or not etched at all. If, as is generally the case, the etch is depth halved for each successive etch cycle, the result is that for n etch cycles, there will be $2^n$ possible different levels in the substrate. Generally n is between 1 and 5. The resulting pattern in the substrate is a quantized version of the desired pattern much like the output of a digital to analog converter, with a quantization level of $MAX/2_n$ where MAX is the maximum value of the waveform.

Usually, the waveform to be synthesized in the binary element substrate is on the order of several wavelengths. For example, a typical binary optical element realization of a lens is generated with as many as 100 wavelengths of curvature. Since the number of etch cycles is generally within the range of from 1 to 5, binary optical elements are generally crated by taking advantage of the fact that an arbitrary delay is optically identical to that delay minus a delay of Mλ, where M is any integer and λ is the optical wavelength of design. This wrapping property allows the designer to compress the lens design by subtracting the largest possible value of Mλ from the wave to be approximated, crating a resulting waveform which ranges from 0 to λ. If the designer then converts this compressed form to a quantized waveform, the binary element is an effective approximation of the desired waveform with a maximum effective error of $2^{-n}\lambda$.

Once the wrapping process has been applied to the desired waveform, it is possible to generate the photolithography masks for the binary optic element. This is accomplished with a successive approximation technique where successive powers of two are subtracted from the desired waveform. Considering that any waveform W that is between 0 and λ may be approximated by $$W(\rho) \cong \lambda \sum_{k=1}^{n} 2^{-k} \omega_k(\rho)$$

where $\omega_k=1$ or 0, the n etching of the etching of the binary optical element may be generated by successively subtracting power of two from the original waveform. Putting this mathematically, if we let $\rho_i = i^{th}$ radial sample $Q_k = K^{th}$ mask, k=1, . . . n we can describe the series of n masks as $$Q_0 = 0$$

$$Q_k = \begin{cases} 0 & \text{(expose) when } W(\rho_i) - \left[\sum_{m=2}^{k} Q_{m-1}(\rho_i) 2^{1-m} \lambda\right] - 2^{-k} \lambda > 0 \\ 1 & \text{(opaque) otherwise} \end{cases}$$

The graph below illustrates the desired waveform and fabricated waveform for a four-level fabrication process with folding over and a step size of λ/4.

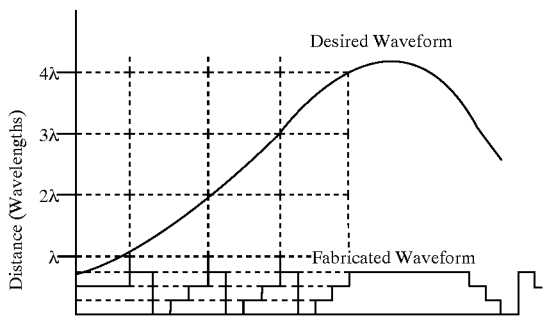

Figure 5:
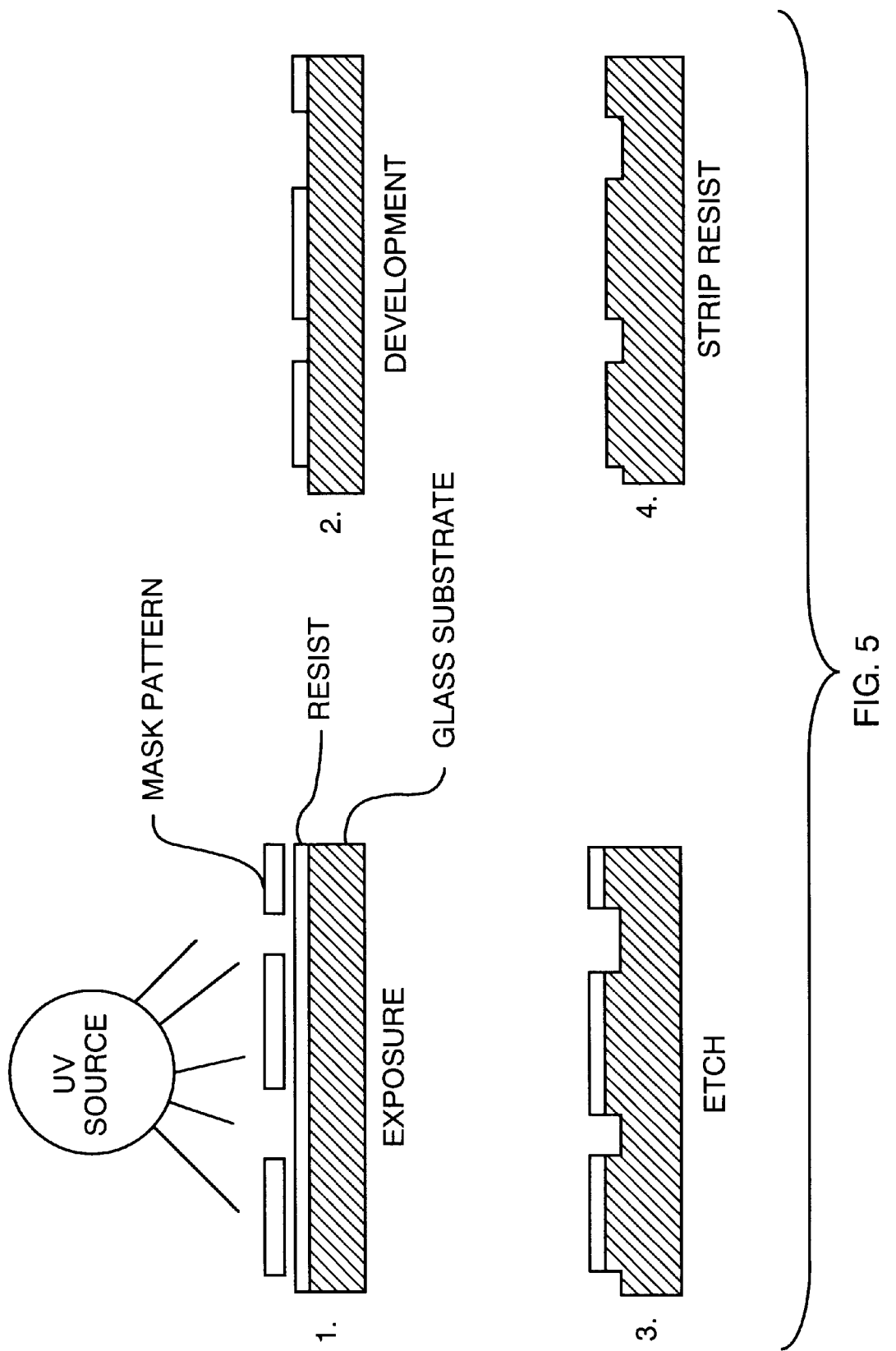
FIG. 5 is a schematic diagram showing a photolithographic process that may be used to form the depth of focus enhancer of FIGS. 2a and 2b.

Photolithography is used to transfer the binary optical waveform onto the substrate. The glass substrate is prepared for this process by carefully cleaning it of contaminants by a wash with acetone and methanol. It is then rinsed with de-ionized water and dried with a jet of dry nitrogen. The process is repeated until the substrate is absolutely clean. Next, a thin layer of photoresist (e.g., 1.3 microns of positive resist, Microposit 1813, Shipley, Inc., Marlborough, Mass.) is spun onto the substrate. The substrate is then placed in a bake oven for half an hour to harden the photoresist for the exposure and develop processes. The resist is then exposed to ultraviolet light through the photolithography mask, placed in close contact with the substrate (See FIG. 5). Next, the photoresist is developed, leaving resist where the mask was opaque (a positive process). The substrate is then placed in an acid etch where the resist protects the underlying area from being etched. The etched depth must be carefully controlled to impart the appropriate phase delay at each location. In general, the delay $W_{glass}$ caused by a step of glass of height $\Delta$ air is $$W_{glass} = \Delta(n_{glass} - n_{air})$$

where $n_{glass}$=glass substrate index of refraction
$n_{air}$=1.0(index of refraction of air)

Using this and the act that mask n is used to create a delay of $2^{-n}\lambda$, the appropriate depth to etch is $$\Delta = \frac{2^{-n}\lambda}{n_{glass} - n_{air}}$$

This etch depth can be imparted to the substrate by characterizing the etch rate for a given etching process and then carefully controlling the etching time. A suitable solution is 5% HF in $NH_4F$. This was found to etch the soda-lime glass slide at 180 nm/min with agitation.

Finally, after the etch, the photoresist is removed with an acetone wash and the substrate is rinsed with de-ionized water. The end product of this processing is a substrate with the mask pattern etched in glass. The substrate may then be sent through further resist-mask-etch cycles to transfer more levels to the phase profile.

The predominant aberration required for depth of focus enhancement is primary spherical, which can be completely described by a fourth-order polynomial. With this in mind, we designed two binary optical elements based on a fourth order polynomial: a two-level element and a four-level element. In general, the fourth order polynomial is of the form:

$$OPD_{Approx} = \gamma\rho^2 + \beta\rho^4$$

which means the phase function associated with this is:

$$\Phi_{approx} = k(\gamma\rho^2 + \beta\rho^4)$$

If we take the first derivative of this, we find that the spatial frequency of the phase is:

$$\Phi_{frequency} = k(2\gamma\rho + 4\beta\rho^3)$$
$$= \frac{2\pi}{\lambda}(2\gamma\rho + 4\beta\rho^3)$$

The size of the phase feature for $\Phi_{approx}$ is the multiplicative inverse of the spatial frequency. Also for a given binary corrector, the phase steps are given by $$\frac{2\pi}{\# \text{Levels}}$$

Multiplying the phase steps by the size of the phase features and scaling the result to the radius of the objective aperture stop, a, we fine that the minimum feature size of the binary element is:

$$S(\rho) = \frac{a\lambda}{(2\gamma\rho + 4\beta\rho^3) \times \# \text{Levels}}$$

Once the parameters $\gamma$ and $\beta$ were computed to generate a useful depth of focus, we found that the misfocus parameter, $\gamma$, could be slightly adjusted to achieve a feature size no smaller than 200 $\mu$m for the two-level element, which simplified fabrication The four-level corrector minimum feature size was no smaller than 100 $\mu$m. Graph (a), below, shows the effective phase profiles of two and four level depth of focus-enhancing elements. Preferably, the four-level enhancer is used.

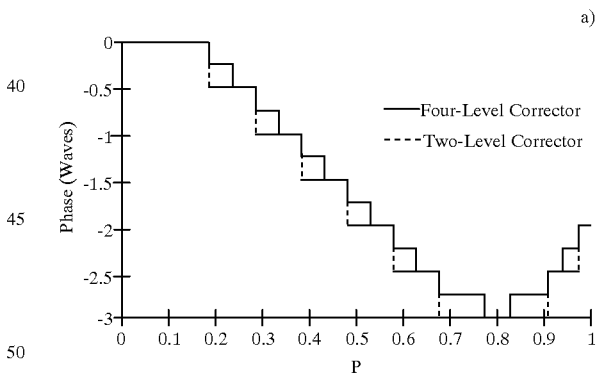

Detection Electronics

Figure 3:
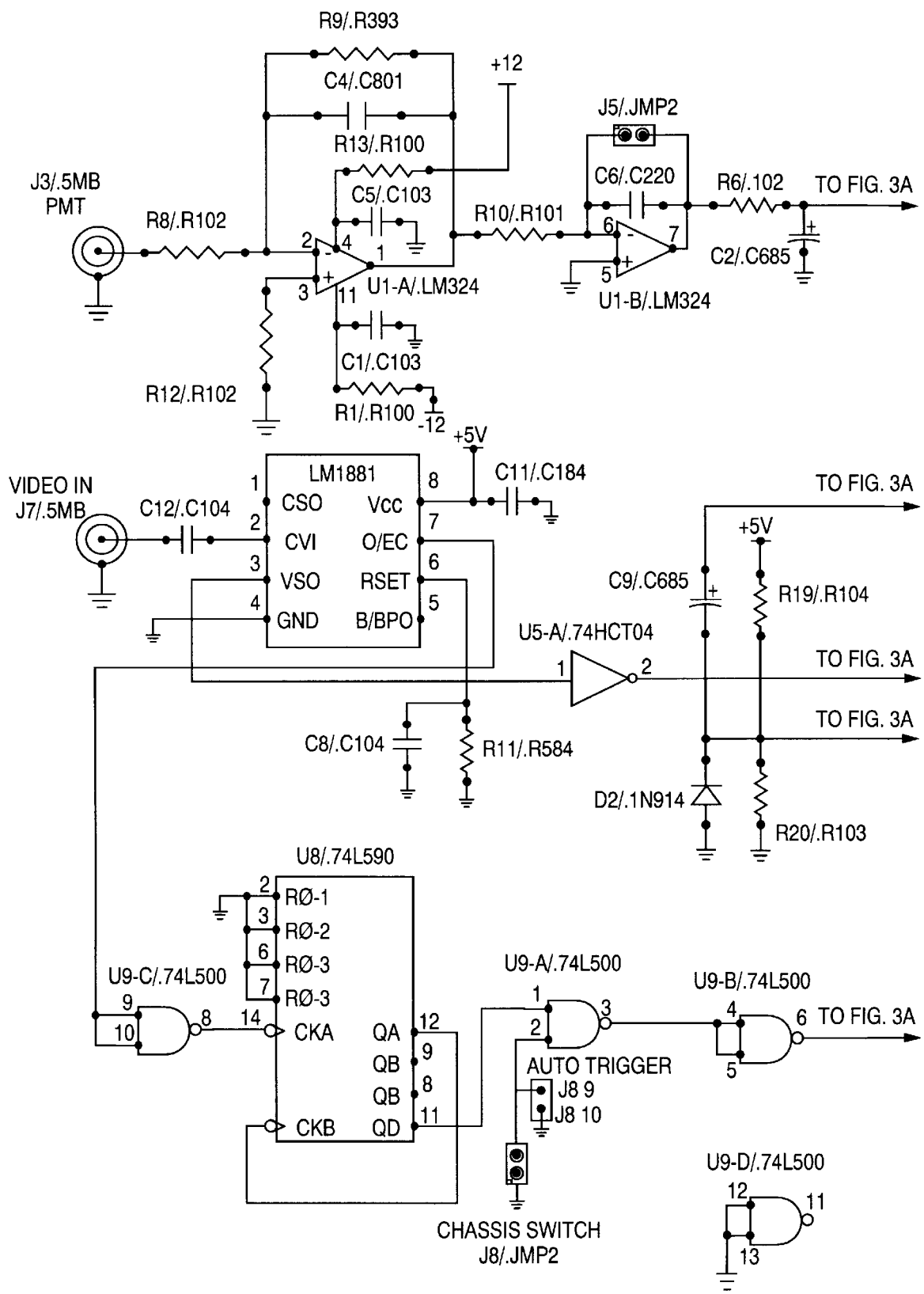
FIGS. 3–3C are a schematic diagram of a circuit that would be suitable for use in triggering the device of FIG. 1.
Figure 3A:
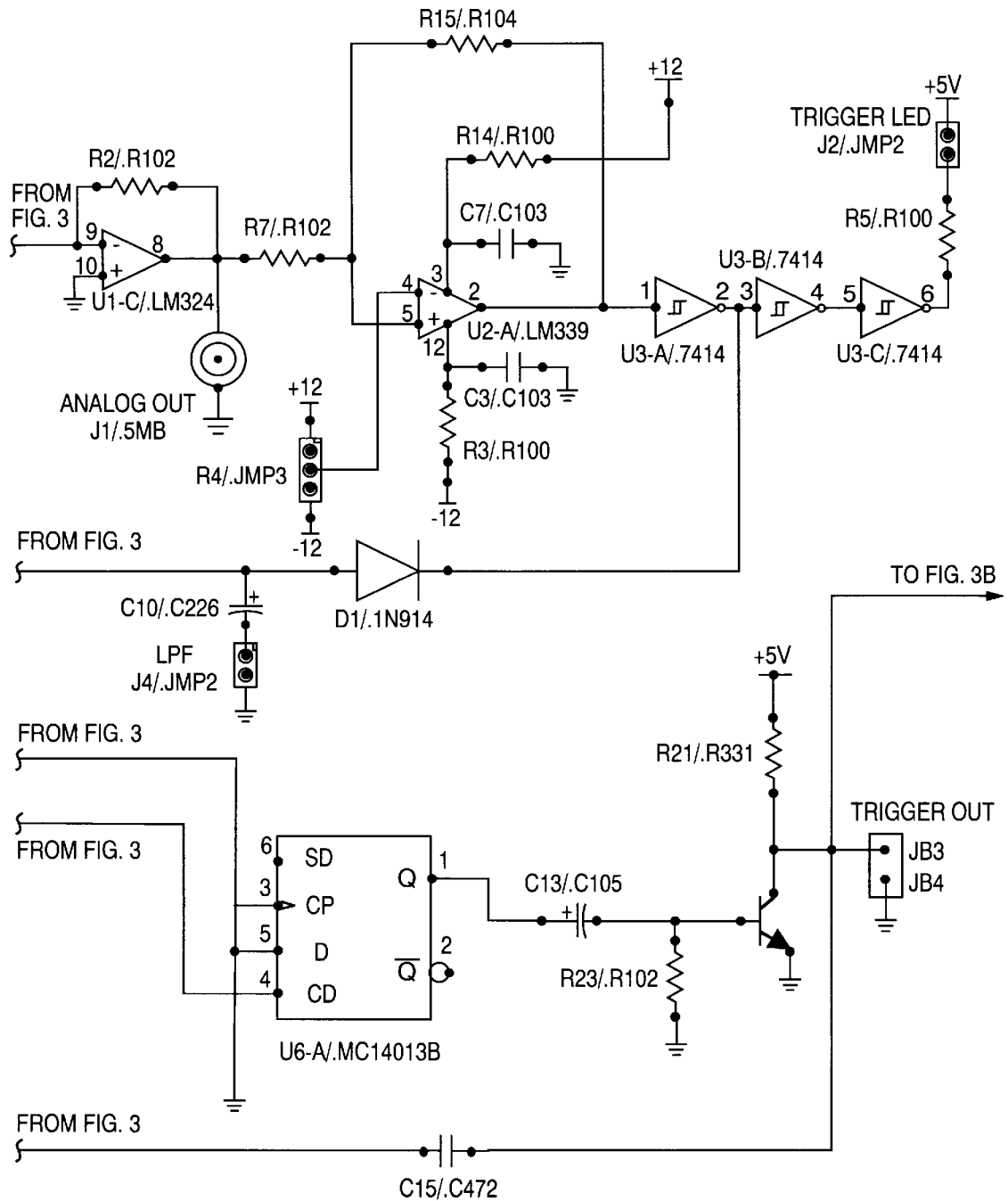
Figure 3B:
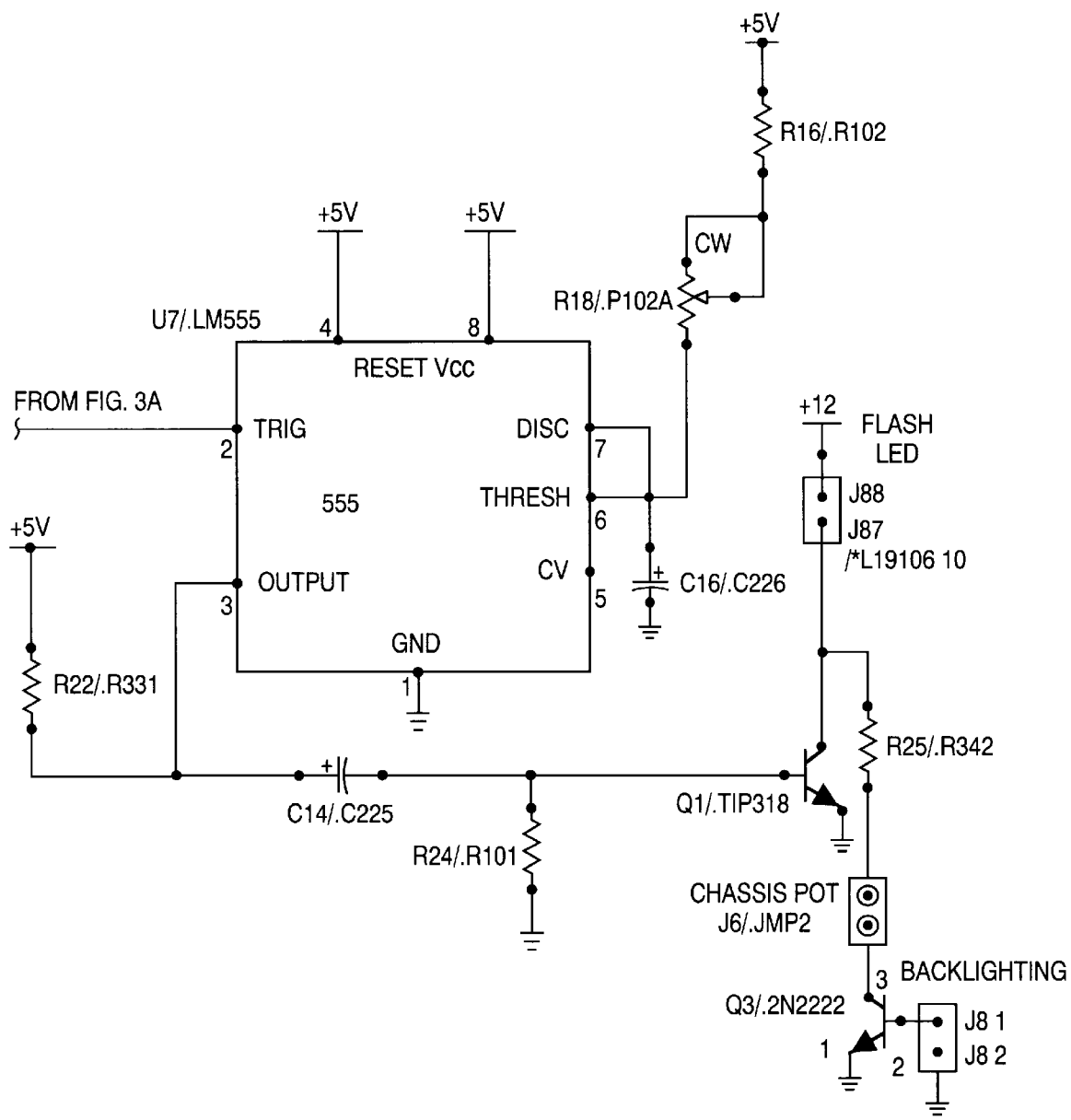
Figure 3C:
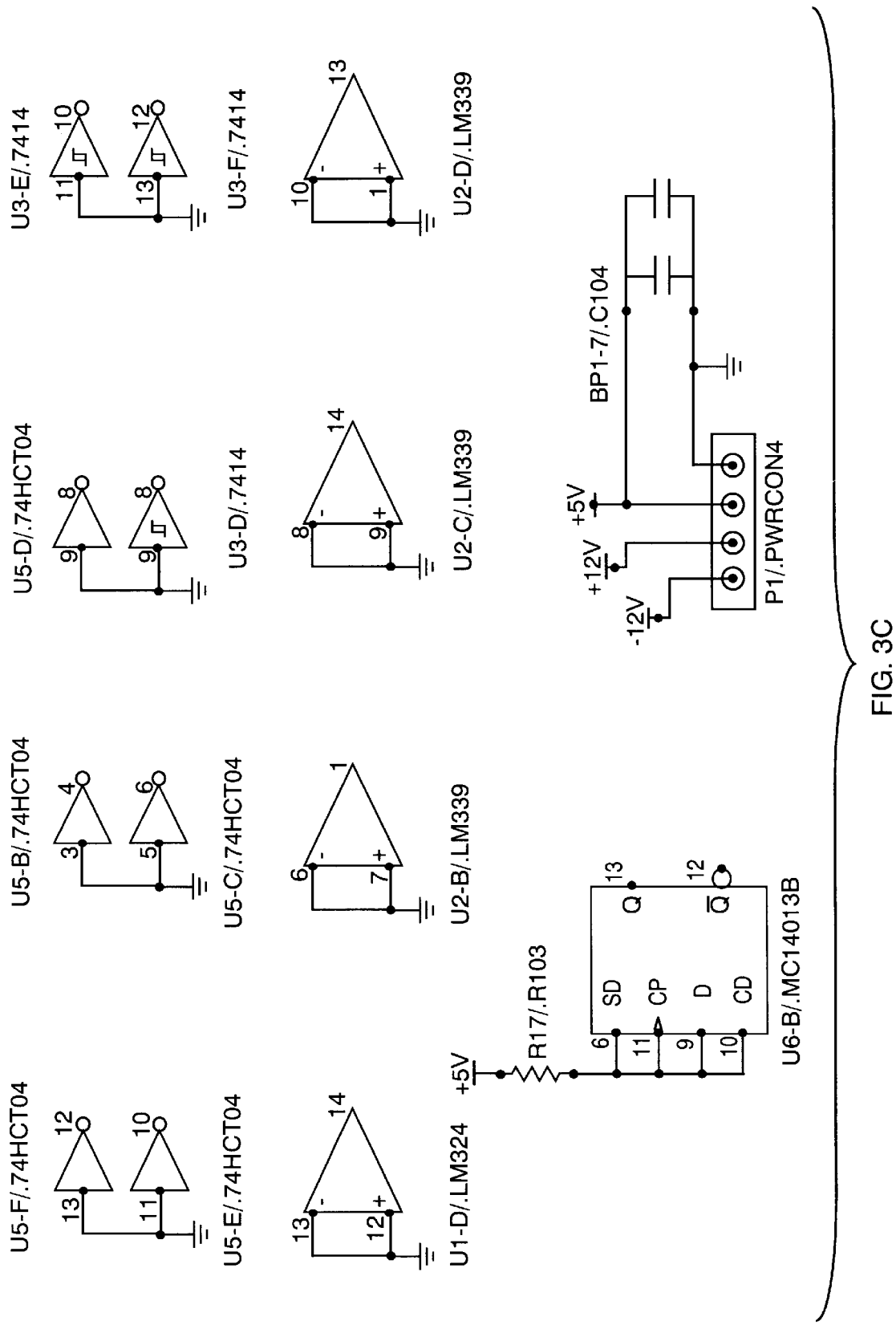

FIG. 3 is a schematic diagram of a circuit that would be suitable for use in triggering the device of FIG. 1. The system light detector signal is amplified by the variable gain circuit comprised of operational amplifier U1. The user may manually adjust the gain of the circuit with the with the potentiometer attached to the terminals at J5. The amplified signal is present for computer analysis at the output labeled "Analog Out." Comparator U2 compares the amplified signal to a threshold set by the potentiometer R4. If t he signal exceeds the threshold, the output of U2 pin 2 goes to logic 1. This value causes the trigger LED to illuminate, alerting the user to the presence of a triggering signal. The trigger also clears flip-flop U6-A pin via U3 and capacitor C9.

Sync stripper U4 provides vertical synchronization signals from the system video camera. These are used to generate synchronized flow chamber LED flashes and computer trigger signals (trigger out). When a vertical synchronization signal arrives from the video camera, the U4 VSO signal sets U6-A pin 1. The transition of U6-A pin 1 forces the transistor Q2 output low via capacitor C13. As C13 charges, Q2 ceases to pull down trigger out The high-low transition of trigger out activates the variable delay output of U7. After a time determined by R18 and R16 and C15, U7's output rises, charging capacitor C14 and temporarily pulling dow pin 7 of J8 which is used to drive the high intensity LED for flow chamber backlighting. Transistor Q3 may be driven by external signals to pull down this same pin 7 under computer and to provide continuous backlighting.

This circuitry assures that a light detector signal (fluoresce or scatter) which may occur at any time results in signals which trigger the computer and LED flash only after the next video vertical synchronization signal. This results in clear images on the video camera and hence, at the computer.

The auto-trigger circuit comprised of U8 and U9 divides the video frame even/odd signal by 10, and if selected by the user switch J9 or computer control line J8, provides a video-synchronized trigger out and LED flash which may be used to randomly sample the flow stream, and also results in clear images.

Imaging and Analysis Software

Figure 4:
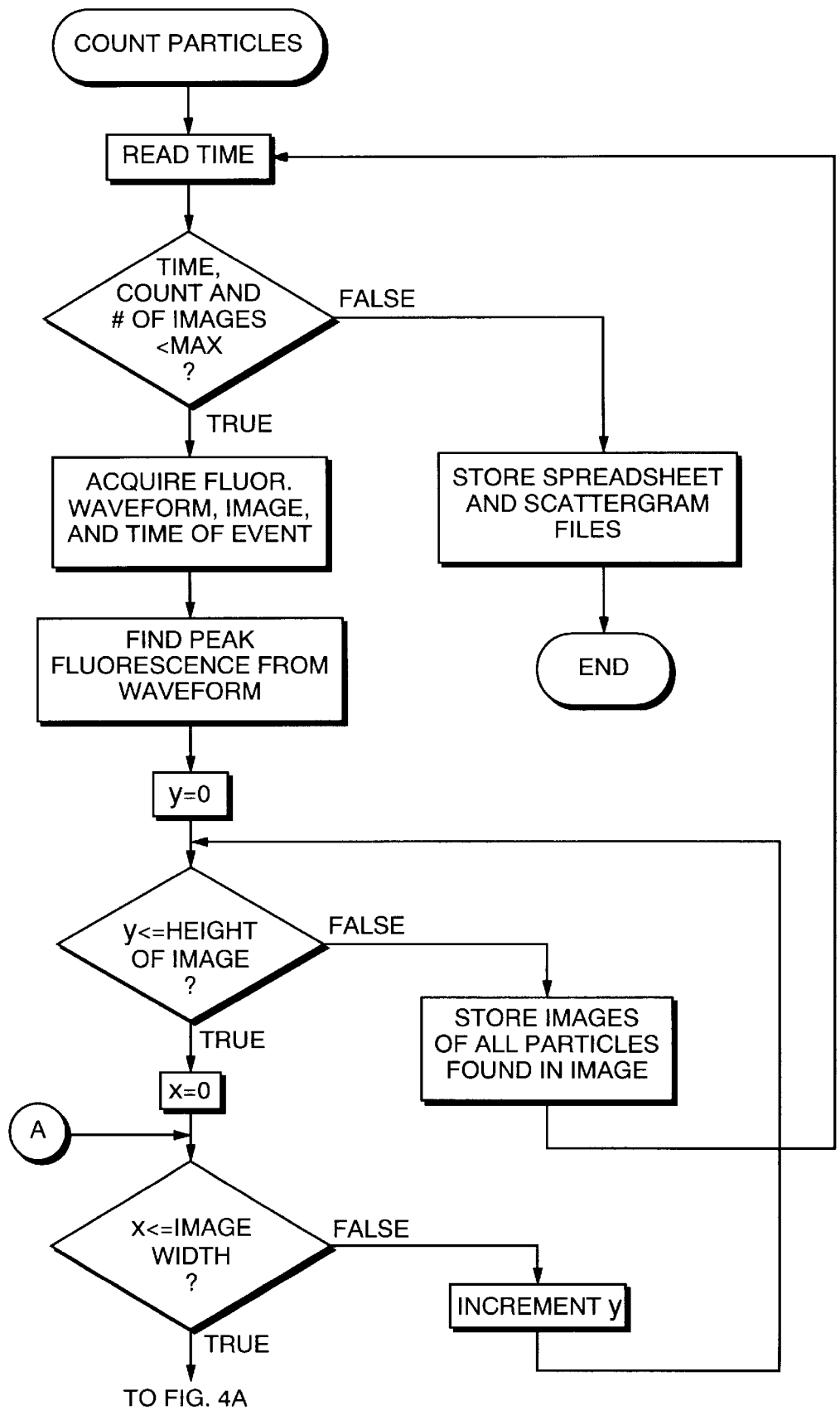
FIGS. 4–4B are flow charts of the algorithms for software suitable for use in the device of FIG. 1.

FIG. 4 is a flow chart of the algorithm for the in-flow particle imaging and analysis system software used by computer 65 to store and analyze images. When a trigger is generated (i.e., a fluorescent or light scattering particle is detected), the software scans the resulting image, separating the different particle sub-images in it. The area of each particle is measured by summing the number of pixels in each particle image below a software selected threshold and multiplying the result by the equivalent physical area of a pixel. This computed area of the particle is stored in a spreadsheet-compatible file along with other properties of the particle, e.g., its measured peak fluorescence, time of particle passage, and the location of the particle in the image. The sub-image of each particle is copied from the chamber image and saved with other sub-images in a collage file. Several of these collage files may be generated for each system experiment. A special system file is generated, containing the collage file location of each particle sub-image, particle size, fluorescence and time of particle passage.

The system software has two data review modes: (1) image collage and (2) interactive scattergram. In the image collage mode, the user may review a series of sub-images in a collage file using the computer mouse to select desired sub-images. Reviewing these files allows the user to identify particle types, count particles, or study other features.

Figure 4A:
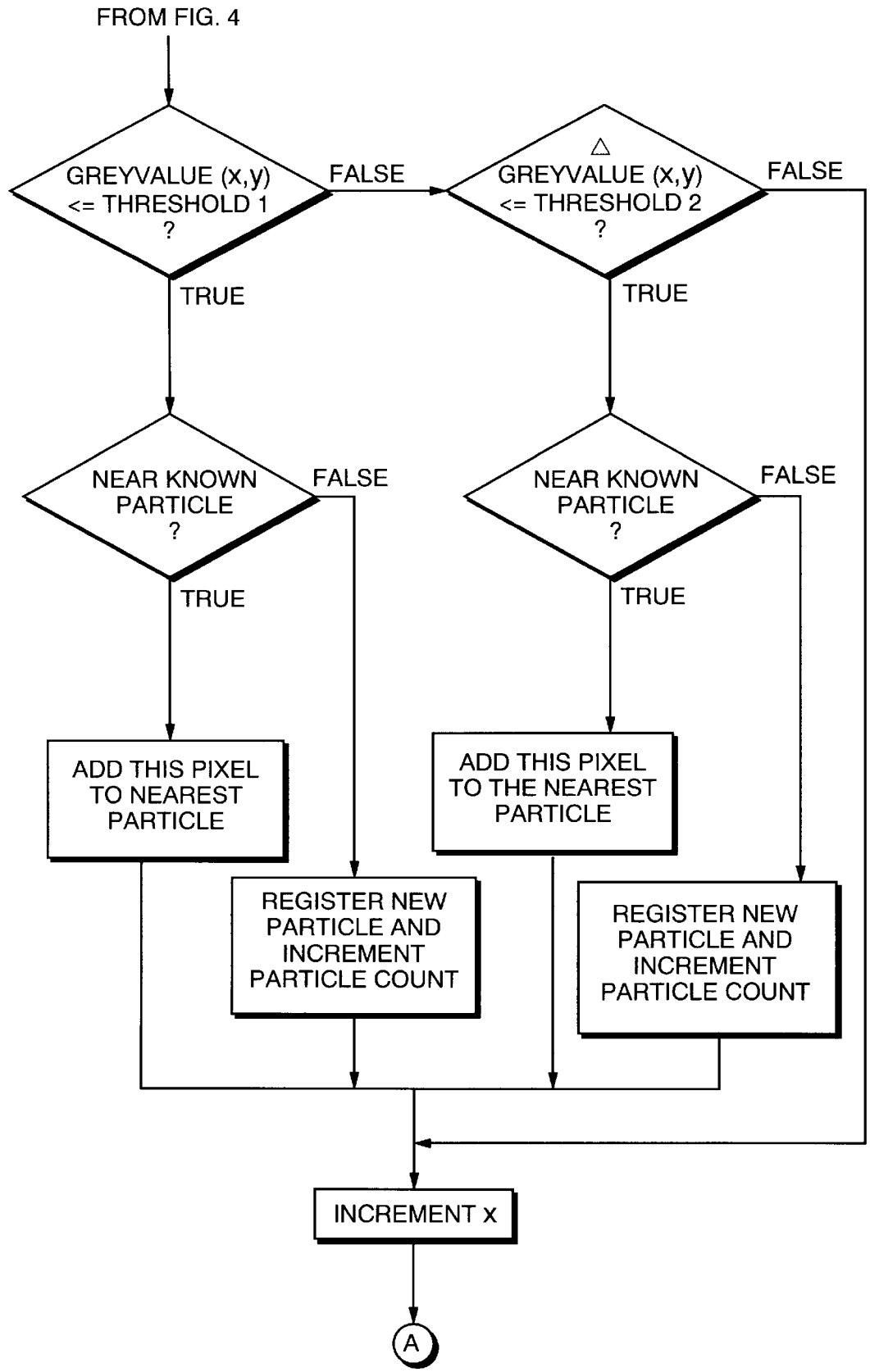
Figure 4B:
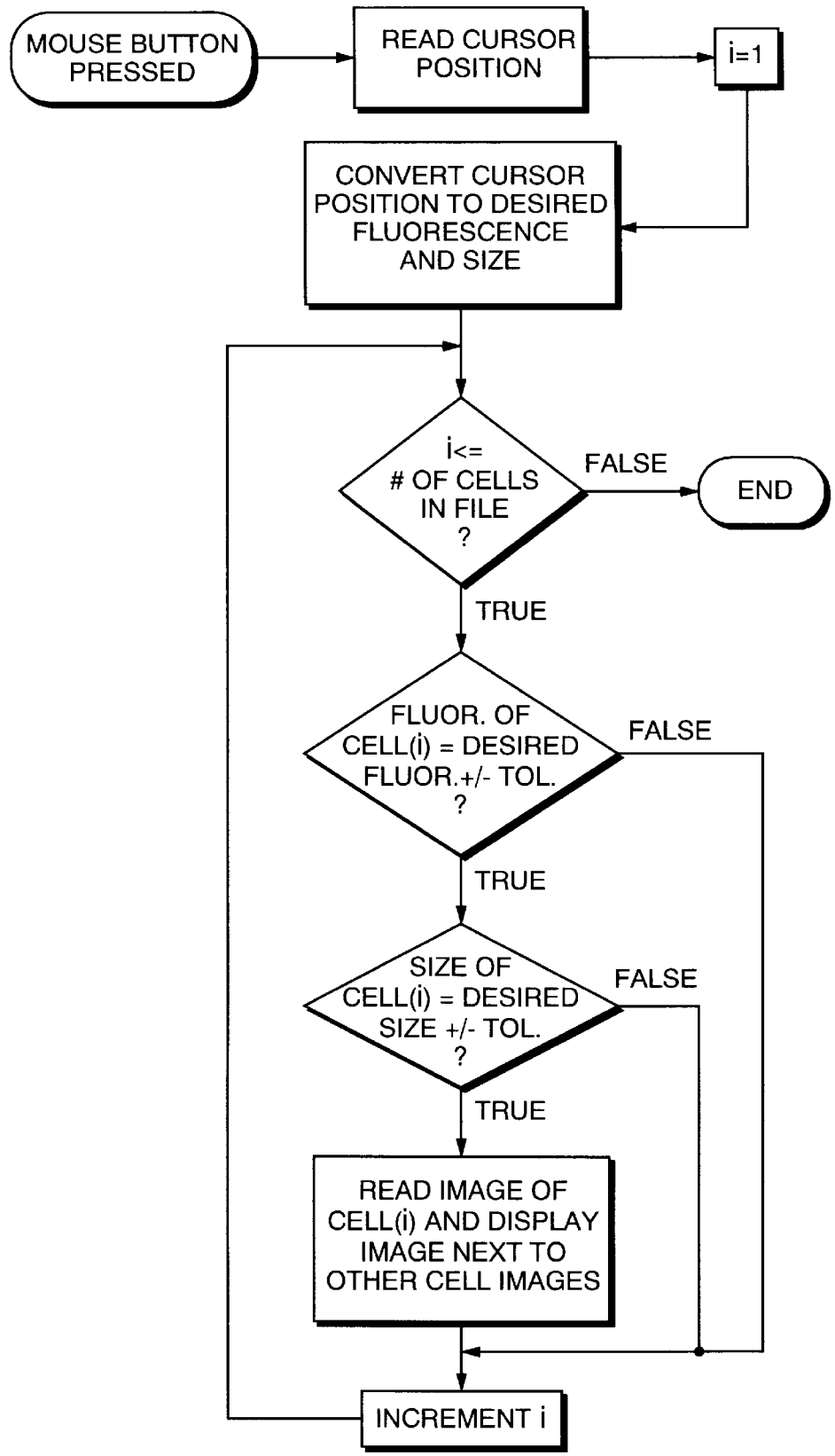

In interactive scattergram mode, data is presented to the user as a dot-plot; e.g., a graph of particle size vs. particle fluorescence or light scatter. As shown by the algorithm in FIG. 4a, if the user selects a region of the scattergram with the computer mouse, images of particles having the characteristics plotted in that region are displayed on the computer screen this allows the user to study particle populations and to examine images of particles with specific sizes or fluorescence, such as cells of a specific type. Because a spreadsheet compatible file is generated for each experiment, the user may also review the data with a spreadsheet program. This information allows the user to readily generate cell counts and fluorescence or scatter and size distribution histograms for each sample. This file also contains the location of each particle in the original image which is used to remove redundant data from particles that have become attached to the flow chamber.

Other embodiments are within the scope of the invention.

What is claimed is:

1. A system for analyzing particles in a fluid, said system comprising:

a flow chamber having a chamber depth for receiving a sample of fluid to be analyzed;

a video system positioned to image particles in the fluid passing through said flow chamber;

imaging optics for focusing light from said flow chamber onto said video system, said imaging optics including a depth of focus enhancer which matches the depth of focus to said chamber depth; and means for storing and analyzing images obtained by said video system.

2. The system of claim 1 further comprising:

a light source arranged to direct excitation light onto said flow chamber; and a detector positioned to detect fluorescence and/or scatter light produced by particles in the fluid passing through said flow chamber, said detector generating a trigger signal whenever fluorescence and/or scatter light is detected, wherein said video system images particles in the fluid passing through said flow chamber in response to said trigger signal.

3. The system of claim 2 further comprising a high intensity light source positioned to backlight said flow chamber in response to said trigger signal.

4. The system of claim 1 wherein said video system automatically images particles in the fluid passing through said flow chamber at a predetermined time interval.

5. The system of claim 4 wherein said predetermined time interval is one second.

6. The system of claim 1 wherein said video system comprises a framegrabber and a video camera.

7. The system of claim 1 wherein said chamber depth is 1 millimeter.

8. The system of claim 1 wherein said depth of focus enhancer is a binary optic element.

9. The system of claim 1 wherein said means for storing and analyzing images includes:

means for displaying an interactive scattergram comprising a graph plotting particle size against particle fluorescence; and means for subsequently displaying the images in a particular region of said scattergram when said region is selected.

10. A method for analyzing particles in a fluid, said method comprising the steps of:

passing a sample of fluid to be analyzed through a flow chamber having a chamber depth;

using imaging optics to focus light from said flow chamber onto a video system, wherein said imaging optics include a depth of focus enhancer which matches the depth of focus to said chamber depth;

imaging particles in said fluid passing through said flow chamber with said video system;

analyzing images obtained by said video system; and storing data obtained in said analyzing step.

11. The method of claim 10 wherein the step of imaging particles in the fluid passing through said flow chamber comprises:

directing excitation light onto said flow chamber, and detecting fluorescence and/or scatter light produced by particles in the fluid passing through said flow chamber;

generating a trigger signal whenever fluorescence and/or scatter light is detected; and imaging particles in the fluid passing through said flow chamber in response to said trigger signal.

12. The method of claim 10 wherein the step of imaging particles in the fluid passing through said flow chamber comprises imaging particles in the in the 3–1000 $\mu$m size range.

13. The method of claims 10 wherein the step of analyzing images obtained by said video system includes determining the size of each imaged particle.

14. The method of claim 10 wherein the step of analyzing images obtained by said video system includes determining the peak fluorescence of each imaged particle.

15. The method of claim 10 wherein the step of analyzing images obtained by said video system includes determining the time of particle passage for each imaged particle.

16. The method of claim 10 wherein the step of analyzing images obtained by said video system includes determining the image location for each imaged particle.

17. The method of claim 10 wherein said step of analyzing images comprises:

displaying an interactive scattergram comprising a graph plotting particle size against particle fluorescence on a display;

selecting a particular region of said scattergram; and displaying the images in said selected region on said display.

* * * * *